United States Patent [19]

Castleman

[11] Patent Number: 4,570,073
[45] Date of Patent: Feb. 11, 1986

[54] METHOD FOR OPERATING AN IONIZATION DETECTOR AND AN APPARATUS UTILIZING THE SAME

[75] Inventor: Bruce W. Castleman, Kenneth City, Fla.

[73] Assignee: Honeywell Inc., Minneapolis, Minn.

[21] Appl. No.: 611,224

[22] Filed: May 16, 1984

[51] Int. Cl.$^4$ .................... G01N 21/00; G01N 23/00
[52] U.S. Cl. ................... 250/432 R; 250/435
[58] Field of Search ............. 250/308, 430, 432 R, 250/435, 428, 438

[56] References Cited

U.S. PATENT DOCUMENTS

| | | | |
|---|---|---|---|
| 3,835,328 | 9/1974 | Harris et al. | 250/432 R |
| 4,053,775 | 10/1977 | Franklin | 250/435 |
| 4,233,126 | 11/1980 | Garcia | 250/435 |

*Primary Examiner*—Bruce C. Anderson
*Attorney, Agent, or Firm*—Mitchell J. Halista; Trevor B. Joike

[57] ABSTRACT

An ionization detector for detecting a vapor constituent uses a first mode of operation in which only the vapor carried by ambient air is conducted through the ionization detector and a second mode of operation in which the outlet line from the ionization detector is connected to direct the exhaust gas flow from the ionization detector through a desiccant cartridge to remove humidity from the gas flow exiting from the ionization detector. The dehumidified gas with the constituent to be detected is then reintroduced into the input of the ionization detector to provide an improved sensitivity of the detector to the constituent. An alternate first and second operating mode cycle is provided to produce an increased output level of constituent detection from the ionization detector. This increased output level can be arranged to initiate an alarm operation for the vapor constituent being detected even at a very low constituent concentration.

10 Claims, 2 Drawing Figures

METHOD FOR OPERATING AN IONIZATION
DETECTOR AND AN APPARATUS UTILIZING
THE SAME

BACKGROUND OF THE INVENTION

1. Field of the Invention

This invention relates to ionization detectors. More specifically, the present invention is directed to a method of operating an ionization detector to improve its sensitivity and an apparatus utilizing the method.

SUMMARY OF THE INVENTION

An object of the present invention is to provide an improved method for operating an ionization detector and an apparatus for utilizing the method.

In accomplishing this and other objects, there has been provided, in accordance with the present invention, a method for operating an ionization detector including the steps of inducing an ambient air flow through the detector in a first mode of operation and inducing a flow of an output from the detector through a dehumidifying means to an input of the detector in a second mode of operation and a detector apparatus comprising constituent detector means for detecting a constituent in a vapor flow, dehumidifying means for removing water from a vapor flow, said dehumidifying means having an outlet connected to an inlet of said detector means, exhaust means for allowing a vapor flow into ambient air, and valve means for selectively directing a vapor from an outlet of said detector means to an inlet of said dehumidifying and to said exhaust means.

BRIEF DESCRIPTION OF THE DRAWINGS

A better understanding of the present invention may be had when the following detailed description is read in connection with the accompanying drawings, in which.

DESCRIPTION OF THE PREFERRED EMBODIMENT

Figure 1:
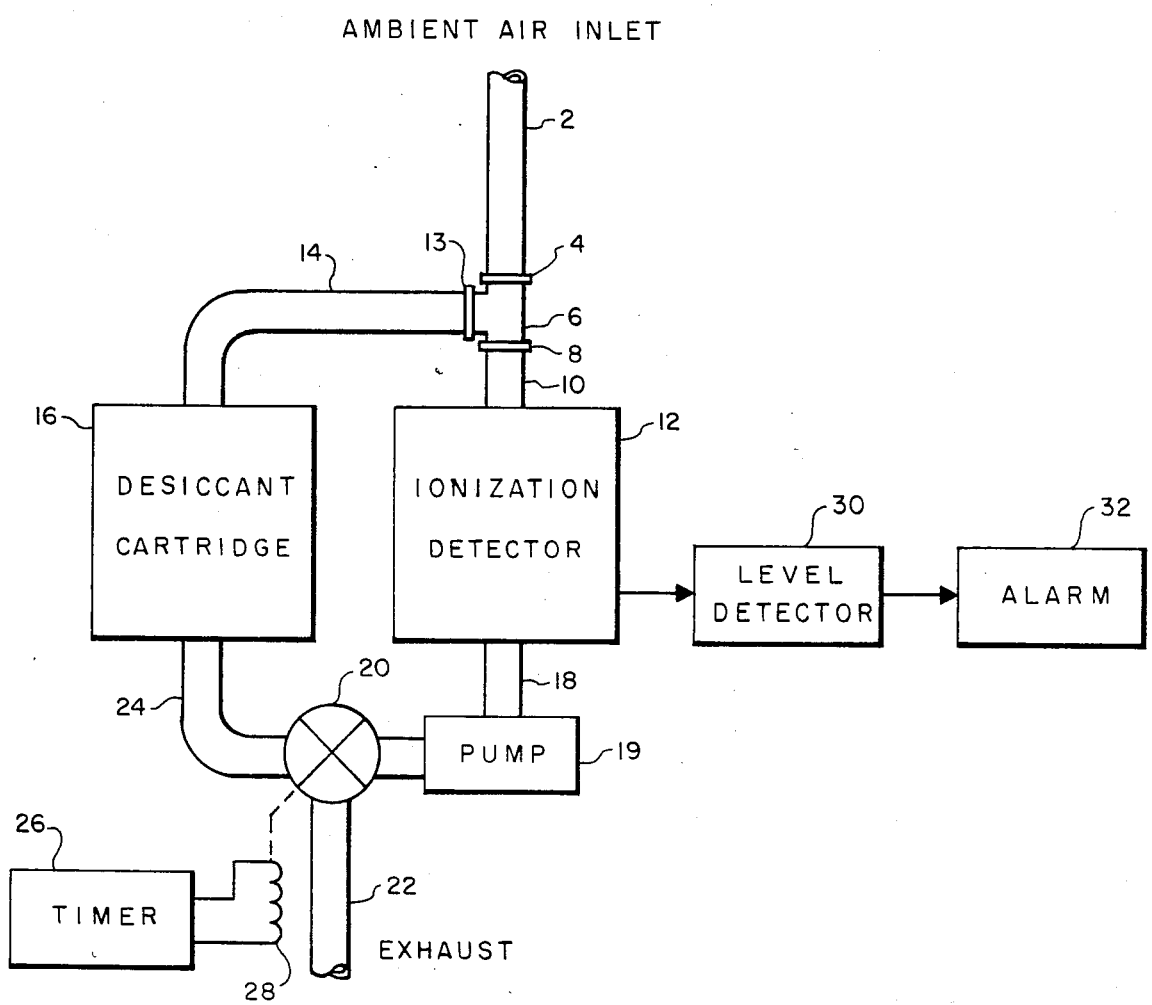
FIG. 1 is a block diagram of an apparatus embodying the method of the present invention and FIG. 2 is an output signal wave shape from the apparatus shown in FIG. 1.

Referring to FIG. 1 in more detail, there is shown an apparatus embodying a method of the present invention for detecting a constituent of an ambient air vapor supplied through an ambient air inlet line 2. The inlet line 2 is connected to a first inlet 4 of a T-connector 6, having an outlet 8 connected to an outlet line 10 which is connected to the inlet of an ionization detector 12. A second inlet 13 of the T-connector 8 is connected by a second inlet line 14 to an outlet of a desiccant cartridge 16. The outlet of the ionization detector 12 is connected by a second outlet line 18 to an inlet of a suction pump 19 which is arranged to urge the flow through the detector 12. An outlet from the pump 19 is connected to an inlet of a solenoid operated 3-way valve 20. One outlet of the valve 20 is connected to an exhaust line 22 and a second outlet of the valve 20 is connected by a third outlet line 24 to an inlet of the cartridge 16. A timer 26 is arranged to periodically operate the valve 20 by means of a valve operating solenoid 28 to selectively direct the flow from the pump 19 to either the exhaust line 22 or the third outlet line 24.

A detector signal output of the ionization detector 12 is connected as an input signal to a level detector 30 which is arranged to selectively operate an alarm 32. The ionization detector may be any well-known ionization detector of the type shown in U.S. Pat. No. 3,835,328. Such detectors successfully detect high concentrations of constituents in ambient air vapors but have a much lower sensitivity when the humidity in the ambient air is at a high level. Such a situation is particularly apparent in the detection of so-called "mustard vapors". By periodically injecting a dehumidified gas flow into the inlet of the detector 12 the system is made substantially more sensitive to the mustard vapors. Specifically, the dehumidified gas flow is injected into the inlet of the detector 12 for a few seconds along with residual mustard vapors to improve the overall system sensitivity. For example, a first mode operation of the detector 12 would be during a 55-second time period wherein only ambient air is passed through the detector 12. This would be followed by a second mode of operation wherein a dehumidified gas flow is introduced into the inlet of the detector for 5-seconds. This cycle would be periodically repeated.

Figure 2:
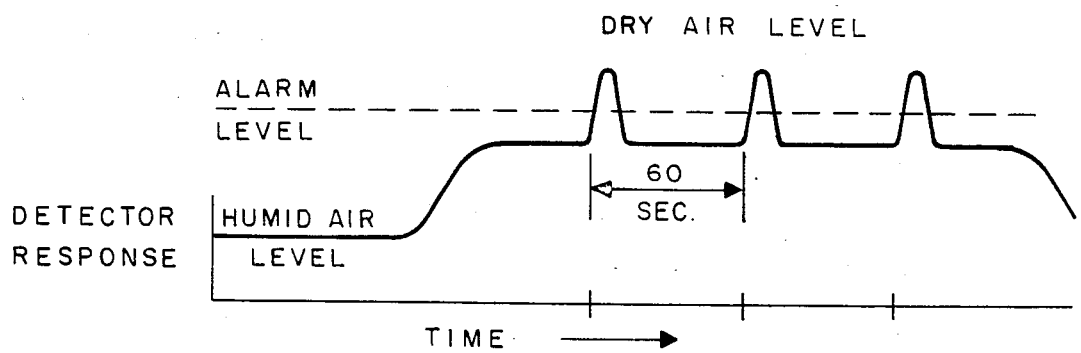

As shown in FIG. 1, the 3-way valve 20 is periodically operated to provide the aforesaid first and second modes of operation by either directing the outlet flow from the detector 12 and the pump 19 to the exhaust line 22 or to the inlet line 24 of the cartridge 16. In FIG. 2, there is shown a typical response utilizing the method of the present invention as embodied in the apparatus shown in FIG. 1. Thus, during the first mode of operation the response of the detector 12 is insufficient to trigger the alarm level of the level detector 30. When the valve 20 is operated by the timer 26 to direct the outlet flow from the detector 12 through the desiccant cartridge 16, there is an immediate increase in sensitivity of the detector 12 to produce an output signal from the detector 12 above the alarm threshold level. This increased output signal is then detected by the level detector 30 to actuate the alarm 32. Such an improved operation allows the detector 12 to detect concentrations of mustard vapors which are much lower than the alarm level concentration in the humidified air required to produce an alarm operation.

Modifications to the embodiment of the invention shown herein may be made by those skilled in the art without departing from the spirit and scope of the present invention. For example, either the valve 20 or a second valve located in line 24 may be used to maintain an exhaust passage at all times to allow a measure of ambient air to be admitted into the detector 12 even during the aforesaid second mode of operation whereby the ambient air carrying the constituent to be detected would be able to enter the detector 12 although in a greatly decreased amount compared to the first mode of operation. Such a modification would enable the dehumidified vapors to be augmented to a degree by the ambient air continuent which, while producing a slight degradation of sensitivity over the operation described above, could provide an increased constituent concentration. Such a secondary exhaust could, of course, be made variable, if desired, to vary the proportion of ambient air admitted to the detector in the second mode of operation.

Accordingly, it may be seen that there has been provided, in accordance with the present invention, an improved method for operating an ionization detector and an apparatus utilizing the same.

The embodiments of the present invention in which an exclusive property or privilege is claimed are defined as follows:

1. Method for operating an ionization detector including the steps of inducing an ambient air flow through the detector in a first mode of operation and inducing a flow of an output from the detector in a first mode of operation and inducing a flow of an output from the detector through a dehumidifying means to an input of the detector in a second mode of operation.

2. A method as set forth in claim 1 wherein the first and second modes of operation are alternate and successive.

3. A method as set forth in claim 1 and including the further step of exhausting the output of the detector in the second mode of operation.

4. A method as set forth in claim 1 and including the further step of comparing an output from the detector to a threshold level to determine an abnormal presence of a constituent in the ambient air.

5. A method as set forth in claim 1 and including the further step of periodically operating a valve means to alternately connect an output of the detector to an exhaust and to an input of the dehumidifying means.

6. An ionization detector apparatus comprising
constituent detector means for detecting a constituent in a vapor flow,
dehumidifying means for removing water from a vapor flow, said dehumidifying means having an outlet connected to an inlet of said ionization detector means,
exhaust means for allowing a vapor flow into ambient air, and
valve means for selectively directing a vapor from an outlet of said ionization detector means to an inlet of said dehumidifying and to said exhaust means.

7. A detector apparatus as set forth in claim 6 wherein said detector means includes a pump means for urging a flow of a vapor carrying the constituent to be detected and an ionization detector for receiving a vapor flow impelled by said pump means.

8. A detector apparatus as set forth in claim 6 wherein said valve means includes a three-way valve.

9. A detector apparatus as set forth in claim 8 wherein said valve means includes a solenoid for selectively operating said valve and a timer means for periodically operating said solenoid to produce the selective directing of said vapor from said detector means by said valve means.

10. A detector apparatus as set forth in claim 1 wherein said detector means includes comparator means for comparing an outpout signal from said detector means with a threshold level to determine a presence of the constituent to be detected.

* * * * *